(12) United States Patent
Noda et al.

(10) Patent No.: US 9,220,532 B2
(45) Date of Patent: Dec. 29, 2015

(54) TRANSLUMENAL PERITONEAL ACCESS AND CATHETER THEREFOR

(75) Inventors: Wayne A. Noda, Mission Viejo, CA (US); Elbert Y. Tzeng, Irvine, CA (US); Stephen Graham Bell, Rome (IT)

(73) Assignee: Minos Medical, Irvine, CA (US)

( * ) Notice: Subject to any disclaimer, the term of this patent is extended or adjusted under 35 U.S.C. 154(b) by 2035 days.

(21) Appl. No.: 12/243,017

(22) Filed: Oct. 1, 2008

(65) Prior Publication Data

US 2009/0088678 A1  Apr. 2, 2009

Related U.S. Application Data

(60) Provisional application No. 60/977,023, filed on Oct. 2, 2007, provisional application No. 61/058,361, filed on Jun. 3, 2008.

(51) Int. Cl.
| | |
|---|---|
| *A61M 5/00* | (2006.01) |
| *A61B 17/34* | (2006.01) |
| *A61B 17/00* | (2006.01) |
| *A61M 25/00* | (2006.01) |

(52) U.S. Cl.
CPC ......... *A61B 17/3478* (2013.01); *A61B 17/3474* (2013.01); *A61B 2017/00278* (2013.01); *A61M 25/0084* (2013.01)

(58) Field of Classification Search
CPC ........... A61B 17/3478; A61B 17/3474; A61B 2017/00278; A61M 25/0084
USPC ............... 604/8–10, 93.01–96.01, 101.01, 604/103.07, 506, 514, 517, 540, 544
See application file for complete search history.

(56) References Cited

U.S. PATENT DOCUMENTS

| | | | |
|---|---|---|---|
| 4,869,717 A | | 9/1989 | Adair |
| 5,484,412 A | * | 1/1996 | Pierpont ................ 604/101.03 |
| 5,810,757 A | * | 9/1998 | Sweezer et al. ............ 604/6.06 |
| 6,156,006 A | * | 12/2000 | Brosens et al. ............. 604/104 |
| 2005/0054994 A1 | | 3/2005 | Cioanta et al. |
| 2005/0165276 A1 | | 7/2005 | Belson et al. |
| 2007/0123840 A1 | | 5/2007 | Cox |
| 2007/0163585 A1 | | 7/2007 | Uesugi et al. |
| 2007/0203517 A1 | * | 8/2007 | Williams et al. ............ 606/191 |

* cited by examiner

*Primary Examiner* — Philip R Wiest
(74) *Attorney, Agent, or Firm* — John L. Rogitz

(57) ABSTRACT

A working cannula is advanced through the urethra into the bladder. Gas is infused through the cannula into the bladder, pressurizing the bladder. A fenestrating shunt catheter is then advanced through the urethra into the bladder and against the wall of the bladder, fenestrating it. A distal segment of the shunt catheter is then advanced through the wall into the peritoneal space, while a more proximal segment of the shunt catheter remains in the bladder. Shunt holes are formed in both the distal segment and more proximal segment so that gas from the pressurized bladder flows through the shunt holes into the peritoneal space, insufflating the peritoneal space.

7 Claims, 3 Drawing Sheets

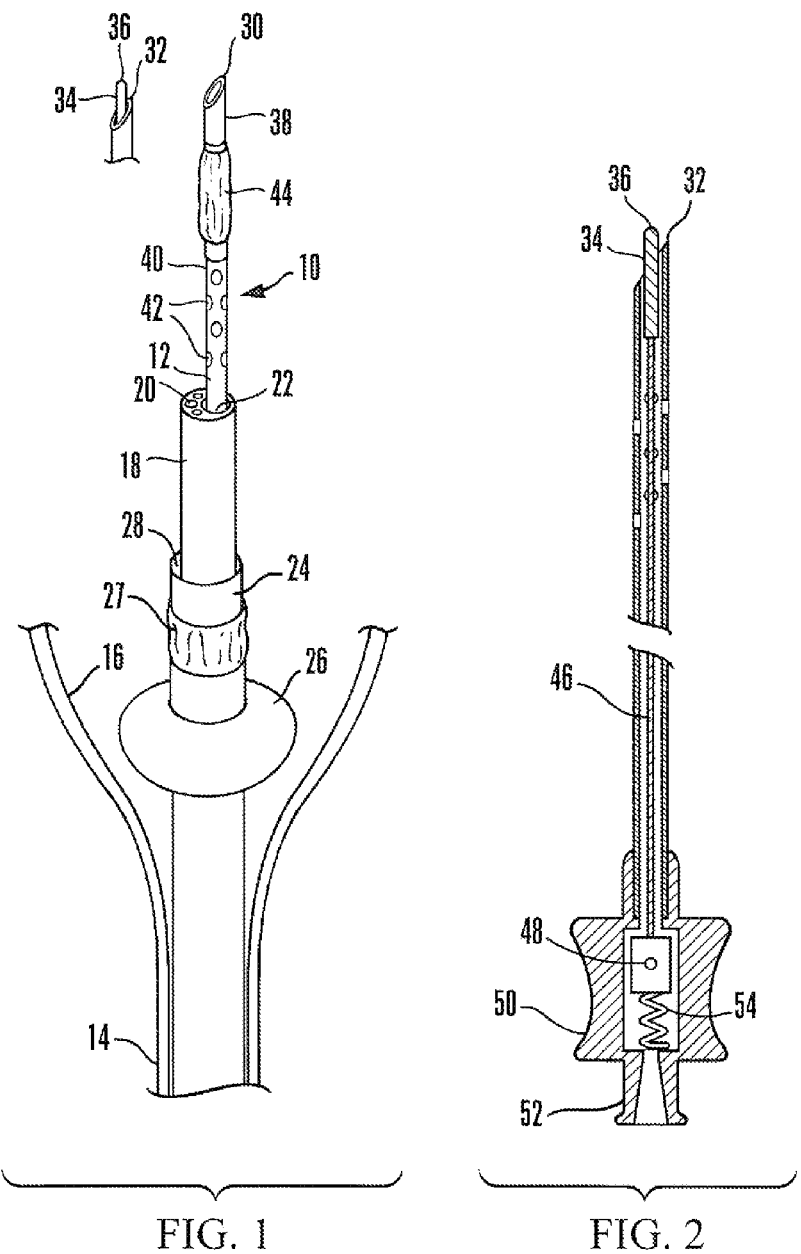

TRANSLUMENAL PERITONEAL ACCESS AND CATHETER THEREFOR

This application claims priority from U.S. provisional patent applications Nos. 60/977,023, filed Oct. 2, 2007 and 61/058,361, filed Jun. 3, 2008.

FIELD OF THE INVENTION

The present application relates generally to access catheters that can be used for translumenal peritoneal access and insufflation.

BACKGROUND OF THE INVENTION

Natural orifice surgery is surgery that is conducted by advancing surgical instruments through the mouth or anus or urethra or vagina. The instruments may be used in some cases to access spaces by fenestrating the walls of interior body structures that are between the natural orifice and the intended surgical site.

Veress needles have been used in the type of non-natural orifice surgery known as laparoscopic surgery to puncture a patient's abdomen and insufflate the peritoneal space for, e.g., removing the gall bladder. Because of this relatively simple application, Veress needles are only a few inches long. Owing to the shortness of the needles, insufflation devices can pump gas through the needles into the abdomen at an acceptably rapid rate.

SUMMARY OF THE INVENTION

As understood herein, to access the peritoneal space by advancing an instrument through a natural orifice into the urethra and fenestrating the bladder wall, a fenestrating/insufflation catheter must be thin enough to fit down the working channel of a flexible endoscope and long enough to reach from the natural orifice to the surgical site, requiring the catheter to have a relatively small bore (e.g., less than 1.5 mm inner diameter) and to be significantly longer (e.g., seventy five centimeters) than a Veress needle. In turn, the present invention understands that gas directed through such a catheter could be expected to undergo a significant pressure drop through the catheter. Because gas must be supplied at pressures that are safely low, the present invention recognizes that significant time can be consumed to insufflate the abdomen through such a catheter.

Accordingly, in example embodiments a relatively large bore working cannula is advanced through a natural orifice (e.g., anus or mouth). In one embodiment the cannula is advanced into the urethra into an organ such as the bladder. Gas is infused through the cannula into the bladder, pressurizing the bladder. A fenestrating shunt catheter is then advanced through the urethra into the bladder and urged against the wall of the bladder, fenestrating it. A distal segment of the shunt catheter is then advanced through the wall into the peritoneal space, while a more proximal segment of the shunt catheter remains in the bladder. Shunt holes are formed in both the distal segment and more proximal segment so that gas from the pressurized bladder flows into the shunt holes in the more proximal segment, to the shunt holes in the distal segment, and out of the shunt holes in the distal segment into the peritoneal space, insufflating the peritoneal space.

In some embodiments the shunt catheter includes an inflatable balloon distally positioned thereon and positionable in a deflated configuration in a hole in the wall of the bladder formed by the shunt catheter. The balloon is inflatable to dilate the hole. The balloon can be proximal to the shunt openings or it can be distal to the shunt openings or it can be disposed between the proximal and distal shunt openings. In other embodiments the balloon is on the introducer cannula. The balloon can have a proximal recess into which an endoscope can nest.

In example embodiments the catheter includes an atraumatic distal tip for fenestrating the wall of the bladder when the distal tip is urged against the wall. In other embodiments the catheter includes a sharp distal tip for fenestrating the wall of the bladder when the sharp distal tip is urged against the wall and a safety plunger with atraumatic tip reciprocatingly juxtaposed with the sharp distal tip between an extended position, wherein the atraumatic tip is located distally beyond the sharp distal tip, and a fenestrating position, wherein the atraumatic tip is located proximal to the sharp distal tip. The safety plunger can be biased to the extended configuration.

In another aspect, an assembly includes an elongated body sufficiently flexible to be advanced through an endoscope and the urethra of a patient into the bladder of the patient. A fenestration element is located at a distal end of the body and is configured to fenestrate a wall of the bladder. A distal segment of the body extends proximally from the fenestration element and a portion of the body extends from the distal segment. At least one shunt opening is formed in the distal segment and at least another shunt opening is formed in the portion of the body that extends from the distal segment to establish fluid communication between a first body cavity in which the distal segment is disposed and a second body cavity in which is disposed the portion of the body extending from the distal segment.

In another aspect, a natural orifice surgery device has an elongated body including a distal segment and a portion extending proximally away from the distal segment. Means are located at a distal end of the body for fenestrating a wall of a bladder of a patient. Also, means are located on the distal segment and on the portion that extends proximally away from the distal segment for establishing fluid communication between a first body cavity in which the distal segment is disposed and a second body cavity in which the portion is disposed.

The details of the present invention, both as to its structure and operation, can best be understood in reference to the accompanying drawings, in which like reference numerals refer to like parts, and in which:

BRIEF DESCRIPTION OF THE DRAWINGS

FIG. 1 is a perspective view showing a natural orifice peritoneal space insufflation assembly in which an example introducer cannula is advanced into a bladder of a patient, an endoscope is advanced though the cannula beyond the open distal end of the cannula, and an example shunt catheter is advanced through the endoscope beyond the open distal end of the endoscope, with proximal portions of the three components removed for clarity and with the distal portion of an alternate fenestration arrangement of the shunt catheter shown for comparison;

FIG. 2 is a cross-section of an example shunt catheter with the alternate fenestration arrangement of FIG. 1;

DETAILED DESCRIPTION OF THE PREFERRED EMBODIMENT

Figure 3:
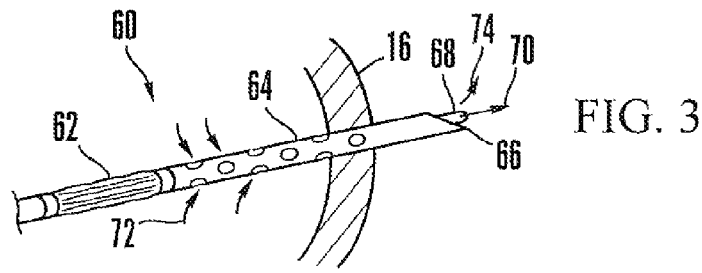
FIG. 3 is a perspective view of the distal portion of an example assembly showing the distal end of the shunt catheter advanced through the wall of the bladder, with proximal portions broken away for clarity.

Referring initially to FIG. 1, a fenestrating/insufflation catheter, generally designated 10, includes an elongated hollow metal or plastic body 12 that is sufficiently flexible for being advanced through a natural orifice into the urethra 14 and bladder 16 of a patient, although the body 12 may also be advanced through a natural orifice such as the mouth into other organs such as the stomach. In non-limiting example implementations the length of the catheter 10 may be between about seventy centimeters and about two hundred centimeters (80 cm-200 cm) and the outer diameter of the catheter 10 may be around two millimeters (2 mm) or smaller. Preferably, the catheter 10 is sufficiently flexible to accommodate an intended steerability of a flexible endoscope 18 through which the catheter 10 can be advanced as shown so that the tip of the endoscope 18 can be directed off axis. It is further preferable in example embodiments that the material of the body 12 provides adequate column strength to transmit the below-described insertion force, prevent kinking, yet be flexible for turning by the endoscope 18. Non-limiting examples of suitable catheter materials include polyvinylchloride, Pebax™, urethane, Teflon™, Peek™, etc.

As shown, the endoscope 18 typically includes one or more optical fibers 20 extending through the endoscope 18 to permit a surgeon to visualize the distal end of the endoscope. At least one working channel 22 typically is provided in the endoscope 18 through which the catheter 10 may be advanced. An introducer cannula 24 may be provided as shown with an inflatable proximal balloon 26 (shown in the inflated configuration) and distal balloon 27 (shown the deflated configuration) attached thereto for anchoring and sealing the cannula in the bladder wall after access has been gained, with the proximal balloon 26 also serving as a stop to prevent over-insertion of the cannula. The endoscope 18 may be advanced through a working channel 28 of the cannula 24 as shown.

As shown in FIG. 1, the fenestrating/insufflation catheter 10 includes a distal 30 that may be open as shown and that is configured for fenestrating the wall of the bladder 16 when the distal end 30 is pushed with sufficient force against the wall. The distal end 30 may be blunt or semi-sharp and by, e.g., a beveled edge configuration as shown, and thus be substantially atraumatic or, as shown at 32 in FIG. 1, it may be sharp, in which case it may be associated with a safety plunger 34 with blunt atraumatic end 36. This latter structure is described further below.

A distal segment 38 of the body 12 extends proximally from the distal end 30. Also, a portion 40 of the body 12 extends proximally from the distal segment. In FIG. 1, the open distal end 30 establishes a shunt opening in the distal segment 38 while plural through-holes 42 in the portion 40 which extend completely through the wall of the portion 40 establish shunt openings, it being understood that additional shunt openings such as holes may also be formed in the distal segment 38 if desired. In any case, with this description in mind it may now be appreciated that by means of the shunt openings, fluid communication is established between a body cavity such as the peritoneum in which the distal segment 38 is disposed and a body cavity such as the bladder 16 in which is disposed the portion 40.

In some example embodiments an inflatable balloon 44 is distally positioned on the catheter body 12. The interior of the balloon 44 communicates with a lumen of the catheter 10 that can be connected to a source of inflation fluid/vacuum to inflate and deflate the balloon in accordance with description below. In the example shown in FIG. 1 the balloon 44 is distal to the shunt openings 42 of the portion 40 of the catheter body 12, although as described below and shown elsewhere herein in other implementations the balloon may be disposed proximally to all shunt openings.

FIG. 2 shows that when the distal end of the catheter is sharp and a safety plunger 34 is provided, in non-limiting example embodiments the plunger 34 may be provided with a rod 46 that extends the length of the catheter to terminate in a thrust bearing 48, which may be disposed in a proximal control handle 50 that remains outside the patient. The handle 50 may be provided with a fitting 52 such as a Luer fitting for establishing fluid communication between a component engageable with the fitting 52 and the interior of the catheter, it being understood that similar control handles and fittings may also be provided for the cannula 24 and endoscope 18 shown in FIG. 1.

A spring 54 is disposed in compression between the handle 50 and thrust bearing 48. Accordingly, the safety plunger 34 with atraumatic tip 36 is reciprocatingly juxtaposed with the sharp distal tip 32 between an extended position, wherein the atraumatic tip 36 is located distally beyond the sharp distal tip 32 (the position shown in FIG. 2), and a fenestrating position, wherein the atraumatic tip 36 is located proximal to the sharp distal tip 32. Because of the spring 54, the safety plunger 34 is biased to the extended configuration.

FIGS. 3-7 illustrate operating principles in accordance with the disclosure herein using an example catheter 60 that in all essential respects is identical to the catheter 10 shown in FIG. 1, except that the catheter 60 includes an inflatable balloon 62 that is proximal to all shunt openings 64 in the catheter. Also, the catheter 60 employs a sharp distal tip 66 with safety plunger 68 that are essentially identical in configuration and operation to those shown in FIG. 2.

Initially, the cannula 24 shown in FIG. 1 is advanced through a natural orifice and the urethra and into the bladder 16 and used as a passageway through which an external source of fluid can infuse fluid such as Carbon Dioxide into the bladder. Owing to the relatively large diameter of the cannula 24 this pressurization of the bladder can be accomplished relatively quickly, on the order of a few minutes or less.

With the bladder pressurized, the endoscope 18 may be advanced through the cannula as shown in FIG. 1 to provide visualization, and then the catheter 60 can be advanced through the endoscope to the wall of the bladder that is adjacent the peritoneum. The distal tip 66 is pushed against and through the wall of the bladder as shown in FIG. 3. The resistance of the wall urges the safety plunger 68 to the fenestrating position until the atraumatic tip of the plunger clears the wall as the tip enters the peritoneum, at which point the above-described spring urges the plunger toward the extended position as indicated by the arrow 70 in FIG. 3 and as shown in FIG. 4.

As can be appreciated from the arrows 72 in FIG. 3, once the distal segment of the catheter 60 enters the peritoneum, fluid in the bladder 16 enters the shunt openings 64 of the portion of the catheter 60 that remains in the bladder and, owing to the pressure difference between the inside of the bladder and the peritoneum, the fluid exits the shunt openings—in this case, the open distal end 66—of the distal segment of the catheter that is in the peritoneum as shown by the arrow 74. The peritoneum thus is insufflated.

Figure 4:
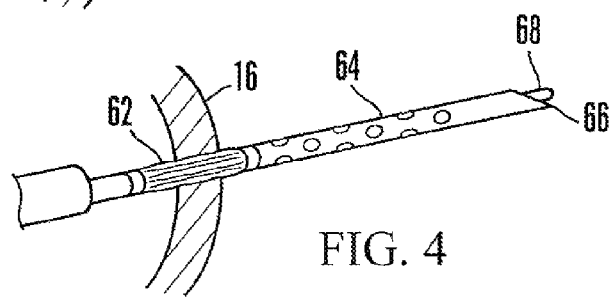
FIG. 4 is a perspective view of the distal portion of the example assembly shown in FIG. 3, showing the balloon in the deflated configuration positioned in the hole in the bladder wall, with proximal portions broken away for clarity.
Figure 5:
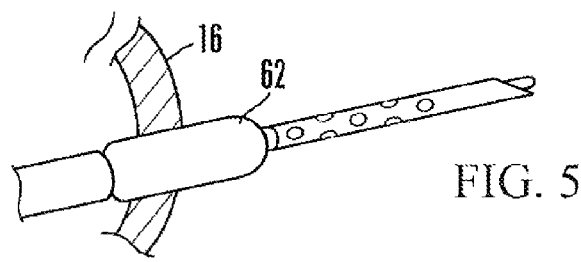
FIG. 5 is a perspective view of the distal portion of the example assembly shown in FIGS. 3 and 4, showing the balloon in the inflated configuration to dilate the hole in the bladder wall, with proximal portions broken away for clarity.
Figure 6:
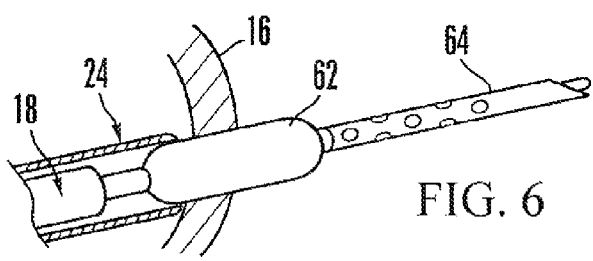
FIG. 6 is a perspective view of the distal portion of the example assembly shown in FIGS. 3-5, showing the dilation balloon positioned in the hole of the bladder wall and the cannula advanced over the balloon, with proximal portions broken away for clarity.
Figure 7:
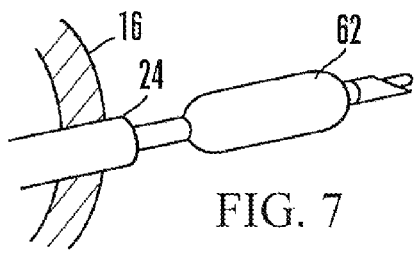
FIG. 7 is a perspective view of the distal portion of the example assembly shown in FIGS. 3-6, showing the introducer cannula positioned in the hole of the bladder wall, with proximal portions broken away for clarity.

After pressure equalizes between the bladder and peritoneum, the catheter 60 is advanced further into the peritoneum as shown in FIG. 4 until the balloon 62 in the deflated configuration is disposed in the hole of the bladder wall that has been made by the catheter 60. The balloon 62 is then inflated as shown in FIG. 5 to enlarge the hole. As shown in FIG. 6, the introducer cannula 24 can slide over the inflated balloon to abut the bladder wall. The catheter 60 with balloon 62 is then pushed further into the peritoneum as shown in FIG. 7 to permit the cannula 24 to be pushed into and through the enlarged bladder wall hole, thereby providing a working channel for operations in the peritoneum once the balloon 62 is deflated and the catheter 60 withdrawn through the cannula.

In alternate embodiments a fenestrating/insufflation catheter can be substantially identical in configuration and operation to the catheters described above except that no insufflation balloon need be provided on the catheter. In such an embodiment, a cannula through which the catheter is advanced can include an inflatable balloon abutting, around, or within the distal segment of the cannula. The cannula balloon may be used to enlarge a hole in an organ wall in accordance with disclosure above. An endoscope may be advanced through the cannula.

Instead of an endoscope, a rigid cystoscope may be used to advance the fenestration/insufflation catheter to provide less of a pressure drop. Once the working cannula has been introduced into the peritoneum, the cystoscope can be exchanged with the flexible endoscope for exploration and therapy.

Figure 8:
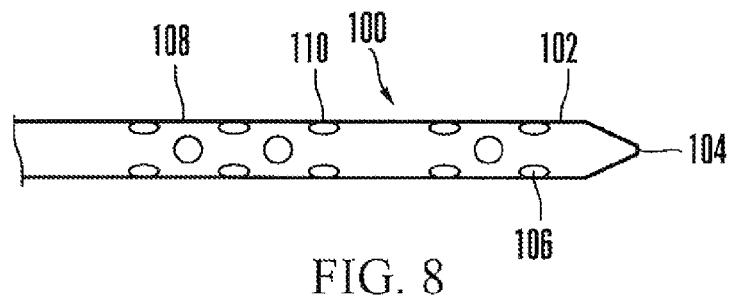
FIG. 8 shows an alternate distal segment that can be used on the shunt catheter.

FIG. 8 shows that a shunt catheter 100 can have a distal segment 102 with closed distal end 104 that may be tapered inwardly toward the distal direction and slightly rounded. The distal segment 102 is formed with shunt openings 106 while a portion 108 proximal to the distal segment 102 is also formed with shunt openings 110 to provide the above-described gas shunting between two body cavities when the wall between the cavities is between the distal segment 102 and portion 108.

Figure 9:
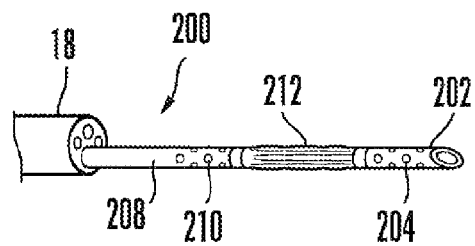
FIG. 9 shows another alternate distal segment that can be used on the shunt catheter.

FIG. 9 shows that a shunt catheter 200 can have a distal segment 202 with distal shunt openings 204. A portion 208 proximal to the distal segment 202 is formed with proximal shunt openings 210 to provide the above-described gas shunting between two body cavities when the wall between the cavities is between the distal segment 202 and portion 208. An inflatable dilation catheter 212 is positioned between the distal shunt openings 204 and proximal shunt openings 210 to operate to dilate an opening formed in the wall of an organ in accordance with principles above.

Figure 10:
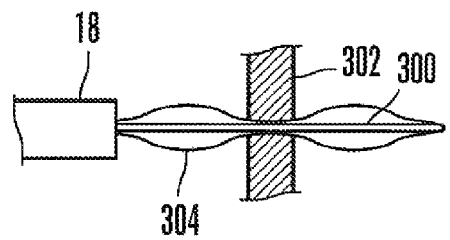
FIG. 10 shows an alternate balloon arrangement with the balloon in the deflated configuration.
Figure 11:
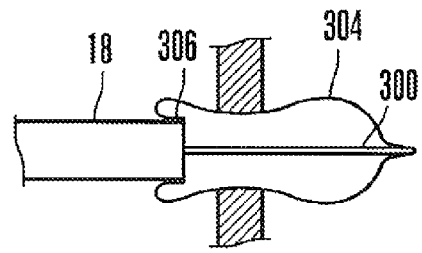
FIG. 11 shows the arrangement of FIG. 11 with the balloon in the inflated configuration.

FIGS. 10 and 11 show a catheter 300 that is in all essential respects identical to any of the above-mentioned catheters for advancement through the wall 302 of an organ such as a bladder, with the following exceptions. An inflatable dilation balloon 304 is positioned on the catheter 300 for enlarging the hole in the wall 302 made by the catheter 300 and is movable between a deflated configuration (FIG. 10), in which the balloon 304 is advanced into the hole, and an inflated configuration (FIG. 11), in which the balloon is inflated while disposed in the organ wall to enlarge the hole. As shown in FIG. 11, with the balloon 304 in the inflated configuration, the endoscope 18 (alternatively, the cannula described above) can be advanced into a proximal recess 306 of the balloon wall. The recess 306 may be established by pushing the endoscope 18 against the proximal end of the balloon 304, or it may be materially formed in the balloon such that when the balloon is inflated the recess 306 automatically is established by the material bias and shape of the balloon. In any case, a smooth transition is afforded from balloon to endoscope (or cannula) so that when the endoscope is pushed distally it smoothly enters the hole in the organ wall following the balloon 304. Endoscope visualization is afforded through the balloon wall.

While the particular TRANSLUMENAL PERITONEAL ACCESS AND CATHETER THEREFOR is herein shown and described in detail, it is to be understood that the subject matter which is encompassed by the present invention is limited only by the claims.

What is claimed is:

1. Assembly comprising:
   an elongated body sufficiently flexible to be advanced through a natural orifice of a patient into the bladder of the patient;
   a fenestration element located at a distal end of the body and configured to fenestrate a wall of the bladder;
   a distal segment of the body extending proximally from the fenestration element;
   a portion of the body extending from the distal segment;
   at least a first shunt opening formed in the distal segment and at least a second shunt opening formed in the portion of the body extending from the distal segment to establish fluid communication between a first body cavity in which the distal segment is disposed and a second body cavity in which is disposed the portion of the body extending from the distal segment; and
   an inflatable balloon distally positioned on the body and positionable in a deflated configuration in a hole in the wall of the bladder, the balloon being inflatable to enlarge the hole, the balloon being a distal-most balloon in that no other balloons are on the assembly distal to the distal-most balloon, the first shunt opening being distal to the distal-most balloon and being at least partially transversely open relative to a long axis defined by the body, the second shunt opening being proximal to the distal-most balloon and being formed through a wall of the portion of the body extending from the distal segment distal to a proximal end of the body, wherein the fenestration element is a distal tip that is closed and tapered.

2. The assembly of claim 1, further comprising an introducer cannula advanceable through the orifice into the second body cavity for infusing fluid into the second body cavity, the elongated body being advanceable through the introducer cannula.

3. The assembly of claim 2, wherein the cannula includes an inflatable balloon distally positioned thereon and positionable in a deflated configuration in a hole in the wall of the bladder, the balloon being inflatable to enlarge the hole.

4. The assembly of claim 1, the distal-most balloon having a proximal recess into which an endoscope can nest.

5. The assembly of claim 1, wherein the fenestration element includes an atraumatic distal tip for fenestrating the wall of the bladder when the distal tip is urged against the wall.

6. The assembly of claim 1, wherein the fenestration element includes a sharp distal tip for fenestrating the wall of the bladder when the sharp distal tip is urged against the wall and a safety plunger with atraumatic tip reciprocatingly juxtaposed with the sharp distal tip between an extended position, wherein the atraumatic tip is located distally beyond the sharp distal tip, and a fenestrating position, wherein the atraumatic tip is located proximal to the sharp distal tip.

7. The assembly of claim 6, wherein the safety plunger is biased to the extended configuration.

* * * * *